(12) United States Patent
Tanaka et al.

(10) Patent No.: US 10,537,310 B2
(45) Date of Patent: Jan. 21, 2020

(54) ULTRASOUND IMAGE CAPTURE DEVICE AND ULTRASOUND IMAGE CAPTURE METHOD

(71) Applicant: HITACHI ALOKA MEDICAL, LTD., Tokyo (JP)

(72) Inventors: Tomohiko Tanaka, Tokyo (JP); Kunio Hashiba, Tokyo (JP); Takashi Okada, Tokyo (JP)

(73) Assignee: HITACHI, LTD., Tokyo (JP)

(*) Notice: Subject to any disclaimer, the term of this patent is extended or adjusted under 35 U.S.C. 154(b) by 1032 days.

(21) Appl. No.: 14/394,893

(22) PCT Filed: Apr. 16, 2013

(86) PCT No.: PCT/JP2013/061325
§ 371 (c)(1),
(2) Date: Oct. 16, 2014

(87) PCT Pub. No.: WO2013/157553
PCT Pub. Date: Oct. 24, 2013

(65) Prior Publication Data
US 2015/0094582 A1     Apr. 2, 2015

(30) Foreign Application Priority Data

Apr. 18, 2012   (JP) ................... 2012-094885

(51) Int. Cl.
*A61B 8/08*     (2006.01)
*A61B 8/06*     (2006.01)
(Continued)

(52) U.S. Cl.
CPC ............ *A61B 8/5223* (2013.01); *A61B 8/06* (2013.01); *A61B 8/14* (2013.01); *A61B 8/463* (2013.01);
(Continued)

(58) Field of Classification Search
CPC ............. G01N 2291/022; G01N 29/24; G01N 2291/044; G01N 29/02; A61B 8/06;
(Continued)

(56) References Cited

U.S. PATENT DOCUMENTS 5,123,417 A * 6/1992 Walker ................ G01S 15/8979
                                                 348/163
2003/0125624 A1* 7/2003 Shiki ...................... A61B 8/06
                                                 600/443
(Continued)

FOREIGN PATENT DOCUMENTS

JP       2003-061958 A    3/2003
JP       2007-195854 A    8/2007
JP       2010-125203 A    6/2010

OTHER PUBLICATIONS

Garcia et al, "Two-Dimensional Intraventricular Flow Mapping by Digital Processing Conventional Color-Doppler Echocardiography Images", IEEE Transactions on Medical Imaging, vol. 29, No. 10, Oct. 2010, pp. 1701-1713.*

(Continued)

*Primary Examiner* — Boniface N Nganga
(74) *Attorney, Agent, or Firm* — Baker Botts L.L.P.

(57) ABSTRACT

The present invention obtains certainty of the blood-flow velocity information that is estimated in the blood-flow mapping display. The signal processor in the ultrasound imager is provided with a Doppler velocity operation part configured to calculate a Doppler velocity from echo signals by using the Doppler effect, and a first blood-flow velocity operation part configured to generate a tissue tomographic image from the echo signals and calculate a blood-flow velocity of a predetermined portion from a motion of the tissue, on the basis of the tissue tomographic image. It is further provided with a second blood-flow velocity operation part configured to calculate the blood-flow velocity of the predetermined portion by using the Doppler velocity calculated by the Doppler velocity operation part. Then, a coincidence degree is calculated between the blood-flow velocity calculated by the first velocity operation part and the blood-flow velocity calculated by the second velocity operation part, as to the predetermined portion, and according to the coincidence degree, certainty/reliability of the blood-flow velocity information is obtained and displayed.

19 Claims, 12 Drawing Sheets

(51) Int. Cl.
  *A61B 8/14*  (2006.01)
  *A61B 8/00*  (2006.01)
  *G01N 29/02* (2006.01)
  *G01N 29/24* (2006.01)

(52) U.S. Cl.
  CPC ........... *A61B 8/5207* (2013.01); *G01N 29/02* (2013.01); *G01N 29/24* (2013.01); *G01N 2291/022* (2013.01); *G01N 2291/044* (2013.01)

(58) Field of Classification Search
  CPC ..... A61B 8/0883; A61B 8/488; A61B 8/5223; A61B 8/5207; A61B 8/463; A61B 8/14; A61B 8/08; A61B 8/00
  USPC .......................................................... 600/441
  See application file for complete search history.

(56) References Cited

U.S. PATENT DOCUMENTS

| | | | | |
|---|---|---|---|---|
| 2006/0025688 | A1* | 2/2006 | Hayase | A61B 8/06 600/454 |
| 2008/0058656 | A1* | 3/2008 | Costello | A61B 5/1107 600/508 |
| 2010/0069757 | A1* | 3/2010 | Yoshikawa | A61B 8/06 600/454 |
| 2012/0265075 | A1* | 10/2012 | Pedrizzetti | A61B 8/06 600/454 |

OTHER PUBLICATIONS

Office Action, dated Oct. 27, 2015, which issued during the prosecution of Japanese Patent Application No. 2014-511222, which corresponds to the present application (with partial English translation attached).

International Preliminary Report for PCT/JP2013/061325, dated Dec. 11, 2014.

Damien Garcia et al., Two-Dimensional Intraventricular Flow Mapping by Digital Processing Conventional Color-Doppler Echocardiography Images, IEEE Transactions on Medical Imaging, Oct. 2010, pp. 1701-1713, vol. 29, No. 10.

* cited by examiner

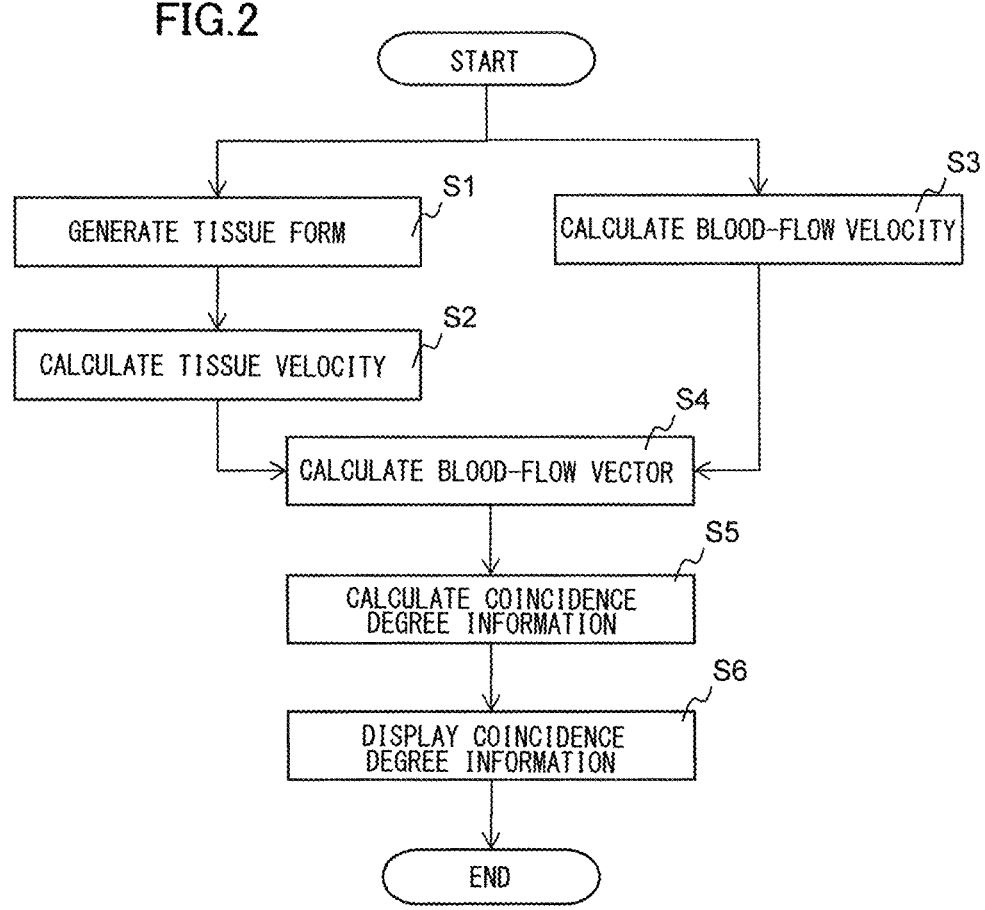

ULTRASOUND IMAGE CAPTURE DEVICE AND ULTRASOUND IMAGE CAPTURE METHOD

TECHNICAL FIELD

The present invention relates to an ultrasound imager for medical use, and more particularly, it relates to an ultrasound imager provided with a function for estimating velocity information of blood flow.

BACKGROUND ART

There is known a blood-flow mapping display method that displays a blood-flow image in a superimposed manner on a tomographic image obtained by an ultrasound imager. A major flow mapping display method includes a color Doppler imaging that identifies a flowing direction and the magnitude of the blood flow by color, and a vector expression that expresses by arrows, or the like, the direction and the magnitude of the blood flow at plural points in the flow. The color Doppler imaging is a method that utilizes the Doppler effect to measure the blood-flow direction with respect to the direction of an ultrasound beam. By way of example, warm hues are assigned to the blood flow in the positive direction, whereas cold hues are assigned to the blood flow in the negative direction, thereby displaying color identification of the blood-flow directions.

However, the color Doppler imaging allows only direct measurement of a velocity component in the ultrasound beam direction, and it is not possible to display the flow direction, that is, in which direction the blood runs within the tomographic view. Considering this situation, it is suggested to estimate a velocity component being orthogonal to the ultrasound beam direction, using an equation of continuity of a two-dimensional flow, and the velocity of the tissue forming a boundary with the blood flow, and obtain a velocity vector from the velocity component being orthogonal to the ultrasound beam direction (Non Patent Document 1). However, actually, the flow is three dimensional, and it is unsure to what extent is reliable the velocity vector that is obtained according to the law of the two-dimensional flow.

The Patent Document 1 suggests a method to calculate a two-dimensional velocity vector by the color Doppler imaging, in order to display velocity variation along the flowing direction of the blood flow, and estimate a passage of the blood flow on the basis of thus calculated two-dimensional velocity vector. There is further disclosed a method that evaluates whether the estimation of the flow passage is proper or not, according to the integrity with nearby data points.

In this method, however, those plural data items nearby, serving as the evaluation standard, are also obtained following the law of the two-dimensional flow.

Therefore, it is unclear whether or not those are certain data items, and this leaves an underlying problem. In other words, even though the flow passage is estimated on the basis of the velocity vector that is evaluated as having high integrity with the nearby data points, the reliability of the flow passage is not necessarily high.

PRIOR ART DOCUMENT

Patent Document

Patent Document 1
Japanese Unexamined Patent Application Publication No. 2010-125203

Non Patent Document

Non Patent Document 1
"Two-Dimensional Intraventricular Flow Mapping by Digital Processing Conventional Color-Doppler Echocardiography Images", IEEE TRANSACTIONS ON MEDICAL IMAGING, Vol. 29, No. 10, October 2010

DISCLOSURE OF THE INVENTION

Problem to be Solved by the Invention

An object of the present invention is to provide an ultrasound imager that accurately evaluates certainty of the blood-flow velocity information being estimated in the blood-flow mapping display, and further displays the certainty, thereby facilitating improvement of ultrasound diagnosis.

Means to Solve the Problem

In order to solve the problem above, the present invention provides a means that formulates certainty and/or reliability of the estimation, with regard to the blood-flow velocity information that is estimated in the blood flow mapping display.

In other words, the ultrasound imager of the present invention is provided with an ultrasound probe configured to transmit an ultrasound wave to an examination target and receive an echo signal reflected from the examination target, a signal processor configured to process the echo signal received by the ultrasound probe, and a monitor configured to display a processing result from the signal processor. Here, the signal processor is provided with an operation part configured to estimate blood-flow velocity information from the echo signal, an image former configured to display blood-flow information by mapping, on the basis of the blood-flow velocity information being estimated, and an estimator configured to obtain certainty of the blood-flow velocity information displayed by the mapping. The estimator formulates the certainty on the basis of the blood-flow velocity information that is obtained by two different methods, for instance.

Effect of the Invention

According to the present invention, there is provided a means to formulate certainty and/or reliability of the blood-flow velocity information that is estimated in the blood flow mapping display, and it is possible to reduce inherent uncertainty included in the reliability due to the blood flow being three dimensional, and provide effective information for examination. This may make a contribution to more reliable diagnosis.

BRIEF DESCRIPTION OF DRAWINGS

FIG. 2 is a flowchart illustrating the operation of the signal processor according to the first embodiment;

EMBODIMENTS OF THE INVENTION

Figure 1:
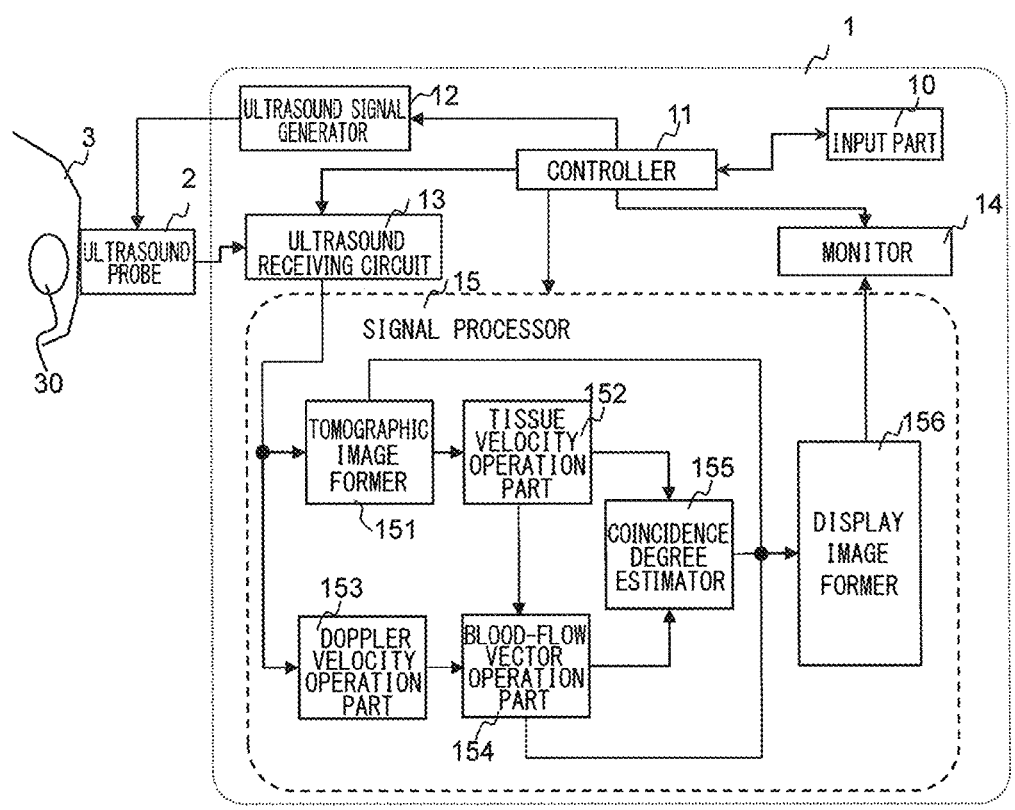
FIG. 1 is a block diagram illustrating a device configuration of the ultrasound imager according to the first embodiment.

Hereinafter, preferred embodiments of the present invention will be explained, with reference to the accompanying drawings. The ultrasound imager 1 of the present embodiment is provided with an ultrasound probe 2 configured to transmit an ultrasound wave to an examination target (3, 30) and receive an echo signal from the examination target, a signal processor 15 configured to process the echo signal received by the ultrasound probe 2, and a monitor 14 configured to display a result of processing by the signal processor 15. The signal processor 15 is characterized in that it is provided with an operation parts (152, 153, and 154) configured to estimate blood-flow velocity information from the echo signal, an image former 156 configured to display blood-flow information by mapping on the basis of the blood-flow velocity information being estimated, and an estimator 155 configured to obtain certainty of the blood-flow velocity information displayed by the mapping. The estimator 155 formulates the certainty, on the basis of the blood-flow velocity information obtained by two different methods, for instance. FIG. 1 is a block diagram illustrating a device configuration example of the ultrasound imager according to the present invention. As shown in FIG. 1, this ultrasound imager has the device main body 1 and the ultrasound probe 2.

The device main body 1 controls the ultrasound probe 2 to generate an ultrasound image, and the device main body is provided with an input part 10, a controller 11, an ultrasound signal generator 12, an ultrasound receiving circuit 13, a monitor 14, and a signal processor 15. The ultrasound probe 2 is brought into contact with a living body (subject) 3, applies an ultrasound wave to a region to be irradiated (irradiation region) 30, according to the signal generated by the ultrasound signal generator 12, and also receives a reflected wave echo signal from the irradiation region 30. The ultrasound probe 2 generates a continuous wave or a pulse wave, depending on a method of scanning.

Constitutional elements of the device main body 1 will be explained. The input part 10 is provided with a keyboard and a pointing device that allow an examiner who manipulates the ultrasound imager to set operating conditions of the ultrasound imager in the controller 11, and the input part also serves as an input part for electrocardiogram signals when an electrocardiogram is used.

The controller 11 controls, the ultrasound signal generator 12, the ultrasound receiving circuit 13, the monitor 14, and the signal processor 15, on the basis of the operating conditions of the ultrasound imager being set via the input part 10, and the controller 11 may be a CPU of a computer system, for instance.

The ultrasound signal generator 12 is provided with an oscillator for generating signals at a predetermined frequency, and transmits a drive signal to the ultrasound probe 2. The ultrasound receiving circuit 13 performs signal processing such as amplification and phasing, for the reflected echo signals received by the ultrasound probe 2. The ultrasound receiving circuit 13 includes a receiving circuit, an envelope demodulating means, and a means for performing Log compression. The monitor 14 outputs the information obtained by the signal processor 15. The signal processor 15 has a function to generate an ultrasound image on the basis of the reflected echo signals from the ultrasound probe 2. Details thereof will be described in the following.

Though not illustrated, the device main body 1 is provided with a scan converter and an A/D converter. The scan converter may be included in the ultrasound receiving circuit 13, or provided in the latter stage of the signal processor 15. When the ultrasound receiving circuit 13 includes the scan converter, there is an advantage that an amount of data treated in the signal processor 15 may be reduced. When the scan converter is not included in the ultrasound receiving circuit 13, the signal processor 15 is allowed to treat a large amount of data, and this may achieve a measuring device with a high degree of precision. The A/D converter may be provided in the former stage of the signal processor 15.

Next, the constitutional elements of the signal processor 15 will be explained in detail. The signal processor 15 is provided with, as major elements relating to the present invention, a tomographic image former 151, a tissue velocity operation part 152, a Doppler velocity operation part 153, a blood-flow vector operation part 154, a coincidence degree estimator (estimator) 155, and a display image former 156.

The tomographic image former 151 forms a B-mode image, for instance, on the basis of the reflected echo signals outputted from the ultrasound receiving circuit 13. Here, the B-mode image may be a tissue form image, being two-dimensional image of an ultrasound irradiation target by using a planar imaging method, or a three-dimensional image by using a volume imaging method. In addition, the tomographic image former 151 extracts positional information of tissue from the tissue morphological image being obtained. The tissue velocity operation part 152 calculates tissue motion information, from plural tissue morphological information items, acquired at different points of time.

The Doppler velocity operation part 153 extracts from the reflected echo signals outputted from the ultrasound receiving circuit 13, for example, a color Doppler mode information, i.e., Doppler blood-flow velocity information of the ultrasound irradiation target, being two-dimensional using the planar imaging method or three-dimensional using the volume imaging method. The blood-flow vector operation part 154 estimates a blood-flow vector through the use of a physical law, from the tissue motion information calculated by the tissue velocity operation part 152, and the Doppler blood-flow velocity information extracted by the Doppler velocity operation part 153. The coincidence degree estimator 155 formulates, through the use of statistical method, the certainty of the blood-flow vector that is estimated by the blood-flow vector operation part 154. The display image former 156 is provided with a memory for storing the reflected echo signals and information in association with the operations in the constitutional elements of the signal processor 15.

Taking the device configuration as described above into consideration, preferred embodiments of the operations of the ultrasound imager will be explained. FIG. 2 illustrates a processing flow of the present embodiment. In FIG. 2, the explanation will be provided assuming, as a specific example, that the portion including the left ventricle is the irradiation region 30 as shown in FIG. 1, but the irradiation region 30 may be a blood vessel or another cardiac cavity, as desired by the examiner.

First Embodiment

<Step S1> (Imaging Step)

Firstly, imaging is performed so as to obtain morphological information (B-mode image) of the irradiation region. In other words, the ultrasound signal generator 12 transmits ultrasound signals at a predetermined frequency to the ultrasound probe 2, and the ultrasound receiving circuit 13 receives echo signals that are applied from the ultrasound probe 2 and reflected from the test subject 3.

The ultrasound frequency of the B-mode image falls into the range from 1 MHz to 20 MHz that enables imaging. A frame rate for taking an image of tissue that fluctuates by cardiac beats, falls into a range equal to or higher than 15 Hz, allowing the cardiac motion to be captured.

The tomographic image former 151 forms from the reflected echoes outputted from the ultrasound receiving circuit 13, for example, a B-mode image, that is, a two-dimensional ultrasound biological image of the ultrasound irradiation target by using the planar imaging method or a three-dimensional ultrasound biological image of the ultrasound irradiation target by using the volume imaging method. At this time, the tomographic image former acquires data items in time series, and forms a time-series ultrasound biological image.

Figure 3A:
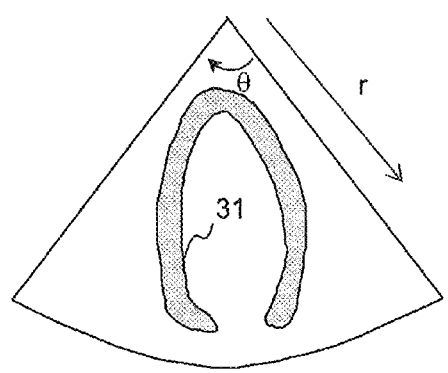
FIG. 3(a) illustrates an image taken by the ultrasound imager and FIG. 3(b) illustrates how to calculate a tissue velocity.

FIG. 3(a) illustrates one example of shape information obtained by the step S1. FIG. 3 illustrates images when a sector probe for performing sector scanning is used as the ultrasound probe 2, setting the left ventricle 31 as an imaging target. For the case of the sector scanning, the depth direction is referred to as "r-direction", and the scanning direction is referred to as "θ-direction".

<Step S2> (Tissue Velocity Calculation Step)

The tomographic image former 151 acquires tissue positional information at a predetermined depth, from the ultrasound biological image formed in the step S1. The tissue position may be determined by detecting a tissue interior wall by image processing. Alternatively, the examiner may designate the tissue interior wall via the input part 10, thereby acquiring the positional information. When the tissue interior wall is detected by the image processing, it is utilized that tissue is recognized as a high-brightness value in the ultrasound image, and a portion with the high-brightness value is assumed as cardiac tissue, thereby acquiring two-dimensional or three-dimensional cardiac tissue position of the portion. When the tissue interior wall is designated by the examiner, the tissue interior wall being an interface between blood and tissue is designated, for instance, via the pointing device provided in the input part 10, thereby giving the position. In the example as shown in FIG. 3, positions a and b are designated, being two tissue interior walls (interface between blood and tissue) at the same depth.

Figure 3B:
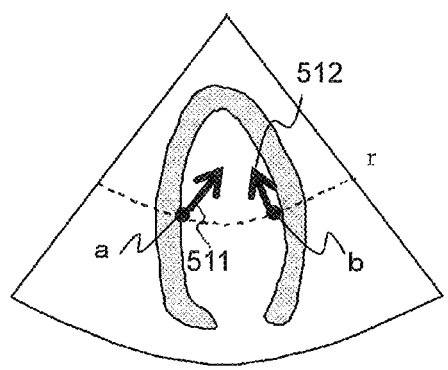

Next, the tissue velocity operation part 152 calculates motion information of the tissue that is located at the designated points at least two. Here, as illustrated in FIG. 3(b), there are obtained as the tissue motion information, tissue blood-flow boundary velocity 511 of the left-side tissue a, and tissue blood-flow boundary velocity 512 of the right-side tissue b. The tissue blood-flow boundary velocity is a speed of the boundary between the tissue and blood, and a velocity of the blood is hydrodynamically equal to a velocity of the tissue on the interface thereof.

As a method for calculating the tissue blood-flow boundary velocity, a pattern matching between two images being temporally continuous may be used, or shifting of the tissue position may be tracked in the temporally continuous images. As a computation technique of the pattern matching, a cross correlation method, SAD (Sum of absolute difference) method, SSD (Sum of Squared Difference) method, or KLT (Kanade-Lucas-Tomasi) method may be employed, for instance. Moved distance of the tissue divided by the image-taking interval is assumed as the tissue blood-flow boundary velocity. The calculation result here corresponds to the velocity on the scan plane as shown in FIG. 3, and the velocity has a velocity component in the r-direction (beam direction) and a velocity component in the θ-direction (a direction orthogonal to the beam direction).

<Step S3> (Blood-Flow Velocity Calculation Step)

Next, the Doppler velocity operation part 153 acquires blood-flow velocity distribution information, focusing on a blood-flow portion within the ultrasound biological image that is obtained by the tomographic image former 151. This calculation is carried out by using a color Doppler imaging being a general method. The blood flow velocity obtained in the step S3 corresponds to the velocity component in the beam direction.

<Step S4> (Blood-Flow Vector Estimation Step)

In the step S4, the blood-flow vector operation part 154 estimates a blood-flow vector, by using the tissue blood-flow boundary velocity (either one of the velocity 511 of the left-side tissue a and the velocity 512 of the right-side tissue b) calculated by the tissue velocity operation part 152, and the blood-flow velocity distribution information acquired by the Doppler velocity operation part 153.

Figure 4:
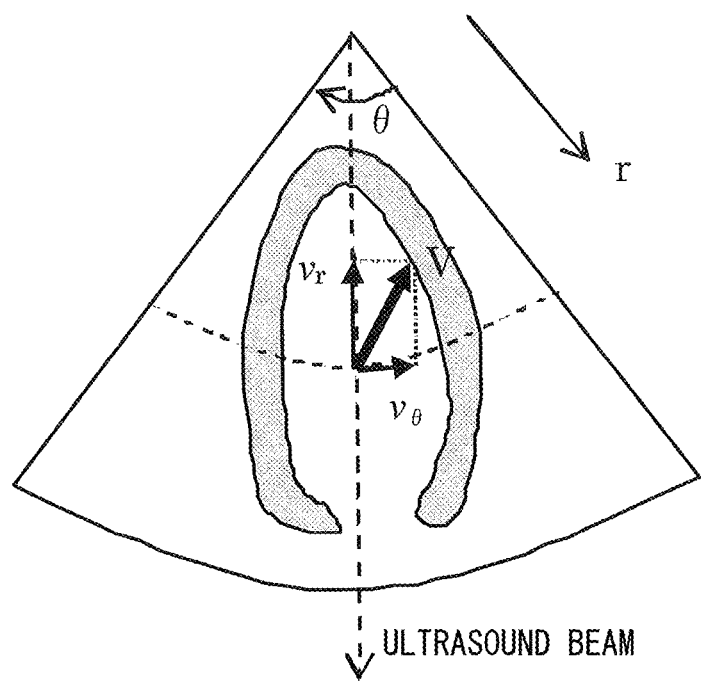
FIG. 4 illustrates a coordinate system.

With reference to FIG. 4, a method for estimating the blood-flow vector will be explained. The velocity measurement using the Doppler effect in the step S3 allows only the velocity $v_r$ to be obtained, being the ultrasound beam direction component of the three-dimensional blood flow velocity V. However, by using the laws of physics, it is possible to estimate the velocity component $v_θ$ in the direction orthogonal to the beam direction (hereinafter, referred to as "orthogonal direction" or "θ-direction"). Here, a polar coordinate system is considered, assuming the depth direction of the ultrasound beams as r-direction, and the sector scanning direction of the ultrasound beams as θ-direction. When the velocity component in the r-direction of blood flow is assumed as $v_r$, and the velocity component in the θ-direction as $v_θ$, the equation of continuity in the polar coordinate system is expressed as the following formula 1, ignoring the effect of blood flow that passes through the imaging plane vertically.

[Formula 1]

$$\frac{v_r}{r} + \frac{\partial v_r}{\partial r} + \frac{1}{r}\frac{\partial v_θ}{\partial θ} = 0 \qquad (1)$$

The formula 1 is also expressed as the formula 2.

[Formula 2]

$$\frac{\partial v_θ}{\partial θ} = -v_r - r\frac{\partial v_r}{\partial r} \qquad (2)$$

According to the formula 2, $v_θ$ is able to be obtained from the formula 3.

[Formula 3]

$$v_\theta(r, \theta) = v_\theta(r) + \int \left(-v_r(r, \theta) - r\frac{\partial v_r(r, \theta)}{\partial r}\right) d\theta \quad (3)$$

Here, $v_\theta(r)$ represents the velocity component in the direction orthogonal to the beam direction of the tissue blood-flow boundary velocity at the depth r, being calculated by the tissue velocity operation part 152 (step S2). It is possible to obtain the velocity vector V(r, θ) from the velocity component $v_\theta(r, \theta)$ in the orthogonal direction obtained by this formula 3, and the velocity component $v_r(r, \theta)$ in the beam direction obtained by the color Doppler imaging in the step S3, along the integral range of formula 3.

Figure 5:
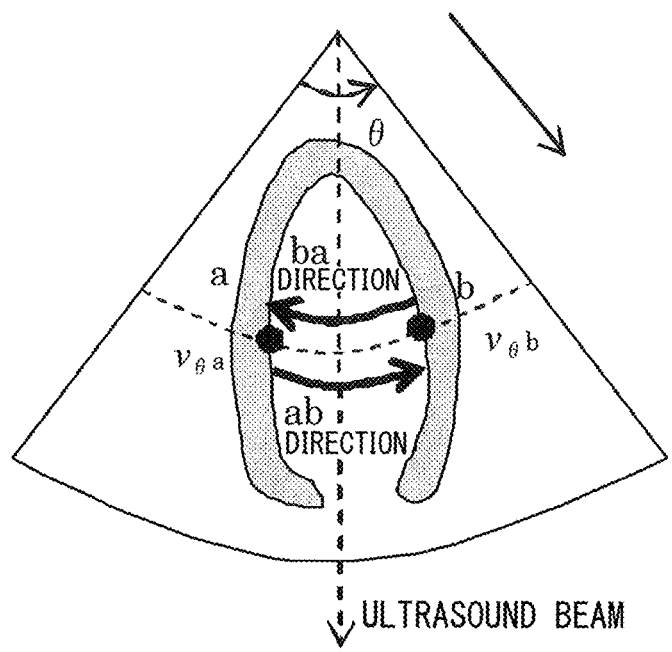
FIG. 5 illustrates how to calculate a blood-flow vector.

As illustrated in FIG. 5, when the integration in the θ-direction in the computation of the formula 3 is performed from the left-side point a to the right-side point b respectively in both cardiac muscle, the velocity in the orthogonal direction at each location from the point a to the point b is expressed as the following:

[Formula 4]

$$v_\theta(r, \theta) = v_{\theta a}^T(r) + \int_a^\theta \left(-v_r(r, \theta) - r\frac{\partial v_r(r, \theta)}{\partial r}\right) d\theta \quad (4)$$

Here, "$v_{\theta a}^T(r)$" represents the velocity component in the θ-direction (direction orthogonal to the beam) of the tissue blood-flow boundary velocity at the point a (depth r) being calculated in the step S2. In contrast, when the integration route is obtained from the opposite tissue interface (point b), it is calculated as the following.

[Formula 5]

$$v_\theta(r, \theta) = v_{\theta b}^T(r) - \int_\theta^b \left(-v_r(r, \theta) - r\frac{\partial v_r(r, \theta)}{\partial r}\right) d\theta \quad (5)$$

Here, "$v_{\theta b}^T(r)$" represents the velocity component in the θ-direction (direction orthogonal to the beam) of the tissue blood-flow boundary velocity at the point b (depth r) being calculated in the step S2.

According to the formula 4 or the formula 5 as described above, it is possible to calculate the velocity component in the θ-direction at each point from the point a to the point b at the same depth. Then, by using the velocity components in the θ-direction and the velocity components in the beam direction obtained in the step S3 (color Doppler imaging), the velocity vector at each point is calculated. The number of points at the same depth corresponds to the number of beams. The display image former 156 described below may display the velocity vector at each point as an image, together with a morphological image.

Calculation for obtaining a degree of coincidence in the next step S5 may use the velocity of the right-side tissue b being estimated by performing the integration of the formula 4 from the point a to the point b, or the velocity of the left-side tissue a being estimated by performing the integration of the formula 5 from the point b to the point a.
<Step S5> (Step for Calculating a Coincidence Degree)

In order to estimate the certainty of the velocity vector calculated in the step S4, a degree of coincidence is evaluated between the tissue blood-flow boundary velocity calculated in the step S2, for instance, the velocity 512 of the right-side tissue b, and the velocity of the right-side tissue b that is calculated by performing the integration of the formula 4 from the point a to the point b. Hereinafter, with reference to FIG. 6, calculation of the coincidence degree will be explained.

Figure 6:
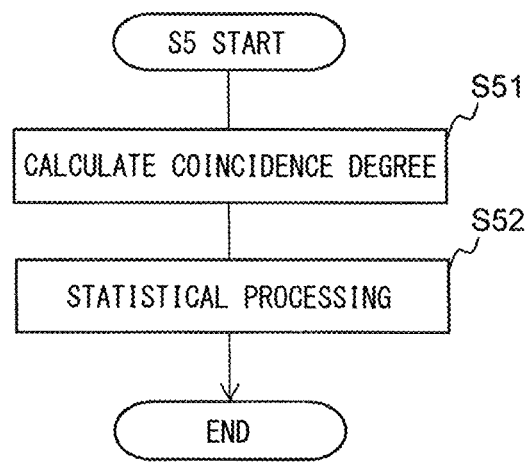
FIG. 6 is a flowchart showing the operation for calculating coincidence degree information.

As illustrated in FIG. 6, calculation of the coincidence degree is made up of two steps; step S51 for calculating the coincidence degree as to each of various depths, and step S52 for apply statistical processing to plural coincidence degrees calculated in S51.
<Step S51>

Calculation of the coincidence degree in the present step is performed by comparing the velocity (the velocity component in the orthogonal direction) obtained in the step S2 (tissue tracking), with the velocity obtained by the formula 4 or the formula 5 in the step S4, with regard to the same location. Here, an explanation will be made as to the case that the coincidence degree between the velocities at the point b (the right-side tissue) shown in FIG. 5 is calculated. The velocity component in the direction orthogonal to the beam calculated in the step S2 is assumed as $v_{\theta b}^T(r)$, and the velocity in the direction orthogonal to the beam obtained in the step S4 is assumed as $v_{\theta b}^m(r)$. If the measurement target is a two-dimensional flow being parallel to the sector scanning plane as shown in FIG. 3, the formula 6 is viable.

[Formula 6]

$$v_{\theta b}^T(r) = v \theta b^m \quad (6)$$

However, in the case of the flow as seen in the left ventricle of the heart, it is three-dimensional, and there is a possibility that the formula 6 is not viable. In view of this, according to the formula 7, a difference therebetween is calculated as the coincidence degree $A_b(r)$, indicating an index that represents a degree of coincidence between both elements, that is, a certainty index indicating the precision of the vector that is calculated in the step S4.

[Formula 7]

$$A_b(r) = v_{\theta b}^T(r) - v_{\theta b}^m(r) \quad (7)$$

It is to be noted that when the velocity is calculated in the step S4, if the integration is performed from the right, not using the formula 4 but using the formula 5, the velocities at the point a are compared, and the coincidence degree is calculated. The coincidence degree $A_a(r)$ in this case is given by the formula 8, as a difference between the velocity component $v_{\theta a}^m(r)$ in the θ-direction at the point a obtained by the formula 5, and the velocity component $v_{\theta a}^T(r)$ calculated in the step S2 in the direction orthogonal to the beam.

[Formula 8]

$$A_a(r) = v_{\theta a}^T(r) - v_{\theta a}^m(r) \quad (8)$$

Instead of calculating the coincidence degree of the blood-flow velocities (velocity components) on the tissue-blood boundary, it is also possible to calculate the coincidence degree at any point on the integration route, by using both the formula 4 and the formula 5.
<Step S51>

Figure 7:
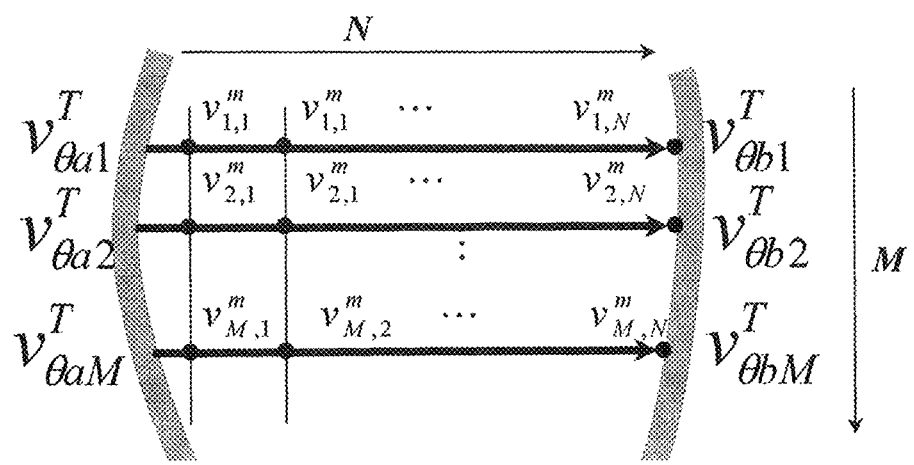
FIG. 7 illustrates data used in a statistical processing.

The coincidence degree calculated in the step S51 may include information regarding the certainty of the blood-flow velocity vector estimation, and in addition, statistical processing may further provide the examiner with easily comprehensible information. In the present step S52, the statistical processing is applied to the coincidence degrees calculated in the step S51. With reference to FIG. 7, the statistical processing performed in the present step will be explained.

The calculation of the blood-flow velocity vector explained in the step S4 is performed on one integration route, but actually, there are generated many integration routes by varying the depth r. When the number of the integration routes is assumed as M, and the number of the blood-flow velocity vectors on the integration routes is assumed as N, blood-flow velocity vectors of M×N points are calculated in the step S4. It is to be noted here that the number N of the blood-flow velocity vectors represents an amount that depends on the number of the ultrasound beams.

When the velocity vectors in the orthogonal direction on the respective points obtained in the step S4 (formula 3) are assumed as $v_{i,j}^m$, and true values of the velocity vectors are assumed as $v_{i,j}^r$, errors in the individual vectors may be expressed as the following:

[Formula 9]

$$\Delta v_{i,j} = v_{i,j}^m - v_{i,j}^r \quad (9)$$

Here, i,j represent the positions in the r-direction and θ-direction (i=1, 2 ... M, j=1, 2 ... N).

The coincidence degree $A_b(r)$ calculated by the step S51 may be expressed by the formula 10 according to integral characteristics, when it is represented as the coincidence degree $A_{b,j}$ of the i-th integration route.

[Formula 10]

$$A_{b,i} = \sum_{j=N} \Delta v_{i,j} \quad (10)$$

The coincidence degree $A_{b,j}$ is calculated as to each of the M integration routes, and an average $E_A$ of thus obtained M coincidence degrees $A_{b,j}$ is obtained by the formula 11.

[Formula 11]

$$E_A = \frac{1}{M} \sum_{i=M} A_{b,i} \quad (11)$$

Figure 8:
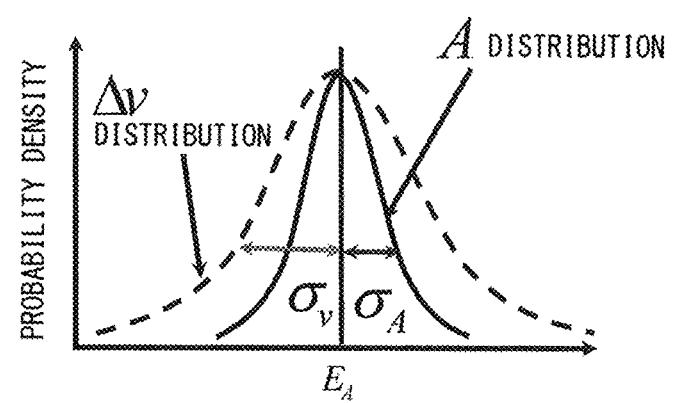
FIG. 8 illustrates the probability density function of the statistical processing.

Here, as shown in FIG. 8, when the dispersion of individual vector errors $\Delta v_{i,j}$ is assumed as $\sigma_v$, and $\Delta v_{i,j}$ holds Gaussian probability density function, it is possible to describe the relations between the dispersion $\sigma_A/N$ of $A_{b,j}/N$ being an average of errors, and $\sigma_v$, as the following according to the central limit theorem.

[Formula 12]

$$\frac{\sigma_A}{N} = \frac{\sigma_v}{\sqrt{N}} \quad (12)$$

In the formula 12, a value of the number N of the blood-flow velocity vectors may be different depending on each integration route, and the value of the number N of the blood-flow velocity vectors may be determined using any of an average value, a maximum value, and a minimum value of the number of the blood-flow velocity vectors in the M integration routes, or a combination of any of those values, that is;

[Formula 13]

$$\sigma_v = \frac{\sigma_A}{\sqrt{N}} \quad (13)$$

According to the formula 11 and the formula 13, the certainty E of each vector calculated in the step S4 is expressed by the formula 14.

[Formula 14]

$$E = E_A \pm t \frac{\sigma_A}{\sqrt{N}} \quad (14)$$

In the formula 14, t represents a value of Student, and it is determined by the value of N. When the value of N is from 20 to 30, commonly used, a practical value of t may be from 1 to 5. When t is 2, the coverage may be 95%.

On the basis of the certainty E calculated in the formula 14, reliability B of the velocity vector being estimated is calculated according to the formula 15.

[Formula 15]

$$B = (E \div U) \times 100 \quad (15)$$

In this formula, U is a representative value of the velocity, and a maximum value, a minimum value, an average, a dispersion of $v_{i,j}$, a combination of any of those values, or a measured velocity range, may be used as the value of U.

<Step S6> (Display Step)

The display image former 156 displays the reliability B obtained as described above on the screen. Various display modes may be available, such as displaying numerical values, displaying with the use of colors, and displaying in the form of comments.

Figure 9:
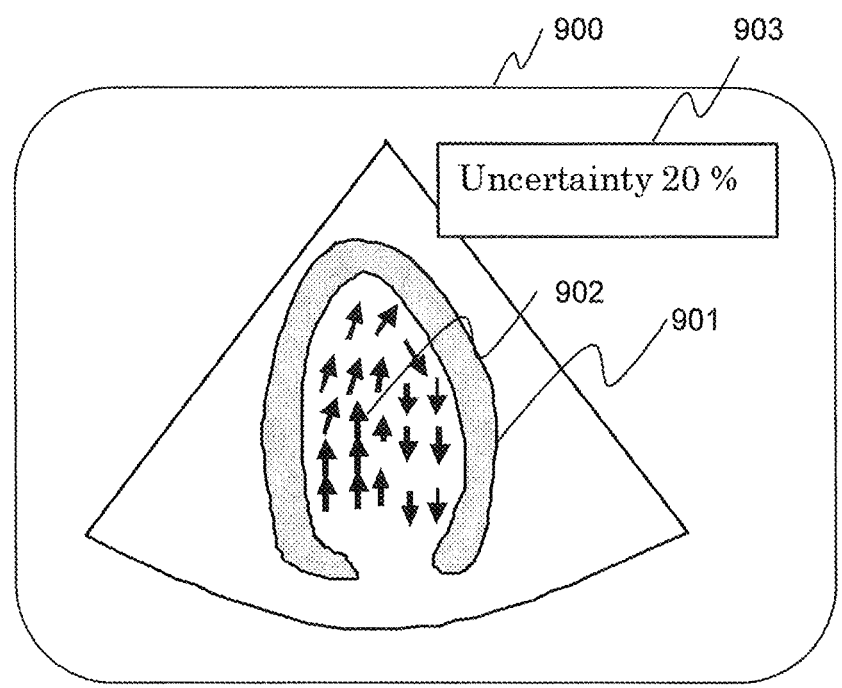
FIG. 9 illustrates one example of a display mode.
Figure 10:
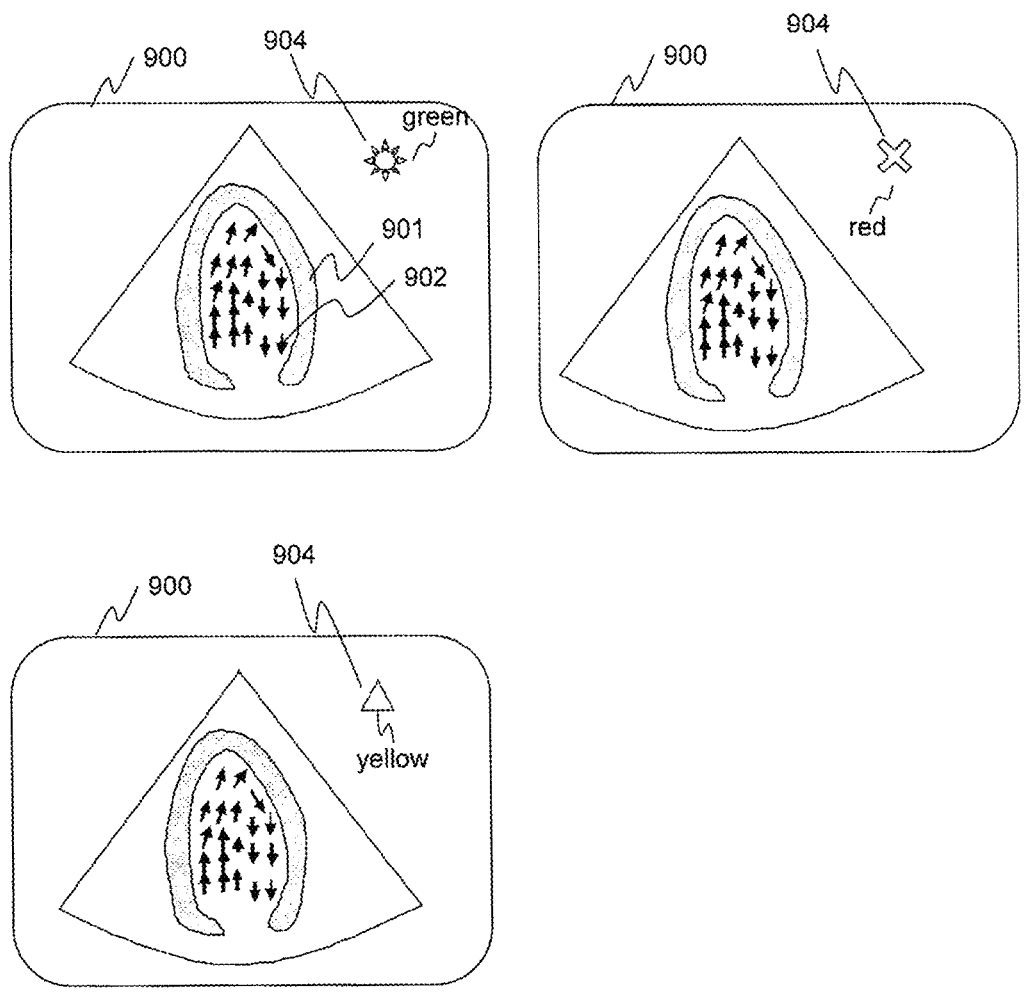
FIG. 10 illustrates alternative examples of the display mode.
Figure 11:
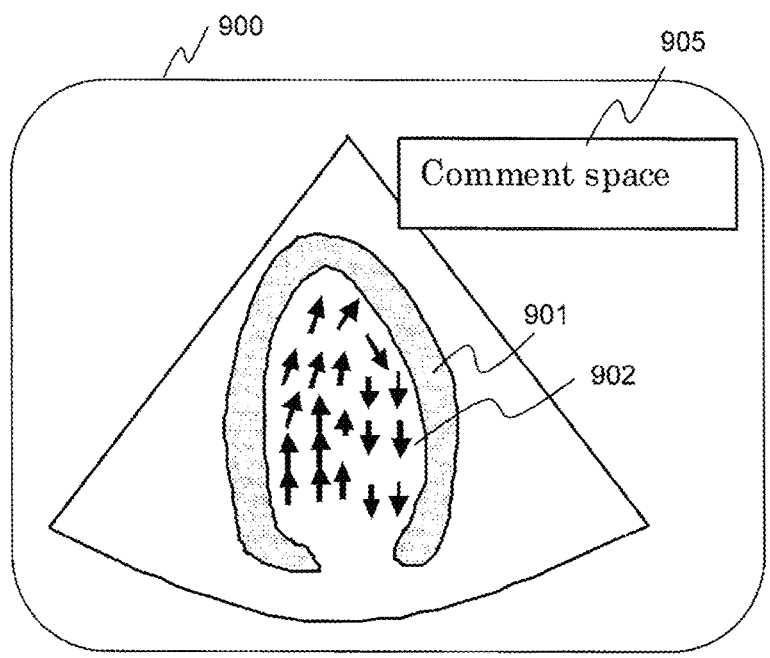
FIG. 11 illustrates a further alternative example of the display mode.

Figures from FIG. 9 to FIG. 11 illustrate display examples of the screen 900. In the example as shown in FIG. 9, the velocity vectors 902 of the blood flow calculated in the step S4 are displayed in a superimposed manner on the monochrome tomographic image 901 formed in the step S1, and the reliability 903 calculated in the aforementioned formula 15 is displayed as a numerical value.

The example as shown in FIG. 10 displays the reliability in the form of lamp 904, together with the monochrome tomographic image 901 and the blood-flow velocity vectors 902. As an example of the color display of the reliability, when the reliability is high, the lamp is green, when attention is needed, the lamp is yellow, and when the reliability is low the lamp is red. This configuration guides the operator to take an image with a high coincidence degree. The level of the reliability is determined depending on whether or not sufficient precision can be obtained to express a clinical difference. By way of example, a threshold of the reliability for each color is set as a default, and the user may be allowed to change the threshold as appropriate.

In the example as shown in FIG. 11, a specific comment 905 is displayed together with the monochrome tomographic image 901 and the blood-flow velocity vectors 902. By way of example, when the coincidence degree is low, a comment is outputted, such as "Coincidence degree is low. Tilt the probe", prompting to improve the coincidence degree. On the other hand, when the coincidence degree is high, a comment such as "Coincidence degree is high" is provided. The criteria for judging the level of reliability for this case is similar to the case of the lamp display.

The display examples as shown in the figures from FIG. 9 to FIG. 11 may be combined as appropriate. For example, it is possible to display a message prompting to perform rescanning, with displaying a numerical value of the reliability or illuminating red lamp, or all of those elements may be displayed.

As described above, the operation of the ultrasound diagnostic apparatus of the first embodiment has been explained with reference to the steps shown in FIG. 2. It is to be noted that the estimation performed in each of the aforementioned steps, the methods used for the calculation, and the index, are just examples, and various modifications are possible.

By way of example, unlike the present embodiment that uses as the coincidence degree, a difference between the velocities respectively obtained by two methods, it is possible to use a ratio between the velocities as expressed by the formula (16-1), a rate of errors as expressed by the formula (16-2), or a combination thereof.

[Formula 16]

$$\frac{v_{\theta b}^{T}(r)}{v_{\theta b}^{m}(r)} \quad (16\text{-}1)$$

$$\frac{v_{\theta b}^{T}(r) - v_{\theta b}^{m}(r)}{v_{\theta b}^{m}(r)} \quad (16\text{-}2)$$

Further in the present embodiment, velocity components in the direction (θ-direction) orthogonal to the beam direction are compared, so as to obtain the coincidence degree. However, it is also possible to compare the magnitude of the velocity vectors. In other words, in the step S4, it is possible to eventually obtain the velocity vector at each point from the velocity component in the θ-direction and the velocity component in the beam direction. Therefore, thus obtained velocity (the absolute value) of the point b and the tissue blood-flow boundary velocity (the absolute value) at the point b being calculated in the step S2 are compared, thereby calculating the coincidence degree between both elements. Also for this case, the coincidence degree may be a difference, a ratio, a rate of error, or any combination thereof.

In the present embodiment, it is explained that the statistical processing of the step S52 uses plural integration routes in the depth direction. The area in the depth direction for this case may cover the entire heart, or it may be limited to a local area such as a cardiac apex, for instance, considering disease or the like, being a diagnostic target. In the present embodiment, the reliability B is further calculated from the certainty E of the estimated vectors, and the reliability B is displayed. However, since the certainty E itself is useful information, it is possible to omit the calculation of the reliability.

Major features of the present embodiment explained above are as the following. The signal processor of the ultrasound imager is provided with, the tissue tomographic image former 151 configured to generate a tissue tomographic image from echo signals, the first velocity operation part (the tissue velocity operation part 152) configured to calculate the first blood flow velocity as to the first portion (e.g., the point a) and the second portion (e.g., the point b), on the basis of the tissue tomographic image that is generated by the tissue tomographic image former, the Doppler velocity operation part 153 configured to calculate the Doppler velocity ($v_r$) from the echo signals by using the Doppler effect, the second velocity operation part (blood-flow vector operation part 154) configured to calculate a second blood flow velocity of the second portion (point b), by using the first blood flow velocity of the first portion (point a) calculated by the first velocity operation part, and the Doppler velocity ($v_r$), and the coincidence degree estimator 155 configured to estimate the coincidence degree between the first blood flow velocity calculated on the second portion and the second blood flow velocity.

The first blood flow velocity corresponds to the tissue blood-flow boundary velocity calculated on the basis of the temporal variation at a tissue position in the tomographic image, and the second blood-flow velocity corresponds to the blood flow velocity that is estimated by using the tissue blood-flow boundary velocity and the Doppler velocity calculated from the echo signals by the Doppler effect.

The coincidence degree estimator 155 applies statistical processing to plural coincidence degrees and calculates the certainty/reliability of the blood flow vector being estimated. In particular, the coincidence degree estimator uses the central limit theorem to calculate the average $E_A$ and the dispersion σ of the plural coincidence degrees, and calculates using these values the certainty E and the reliability B of the vector.

According to the present embodiment, the statistical processing is performed on the coincidence degrees between the velocity calculated by the morphological tracking method for tracking the morphology movement, and the velocity estimated by the color Doppler imaging, thereby the certainty/reliability of the blood-flow velocity information that is estimated in the blood flow mapping display is calculated and displayed. Thus, the examiner is able to be provided with an index being suitable for obtaining an accurate examination result.

Next, another embodiment with an additional feature will be explained, using the first embodiment as a base.

Second Embodiment

Figure 12:
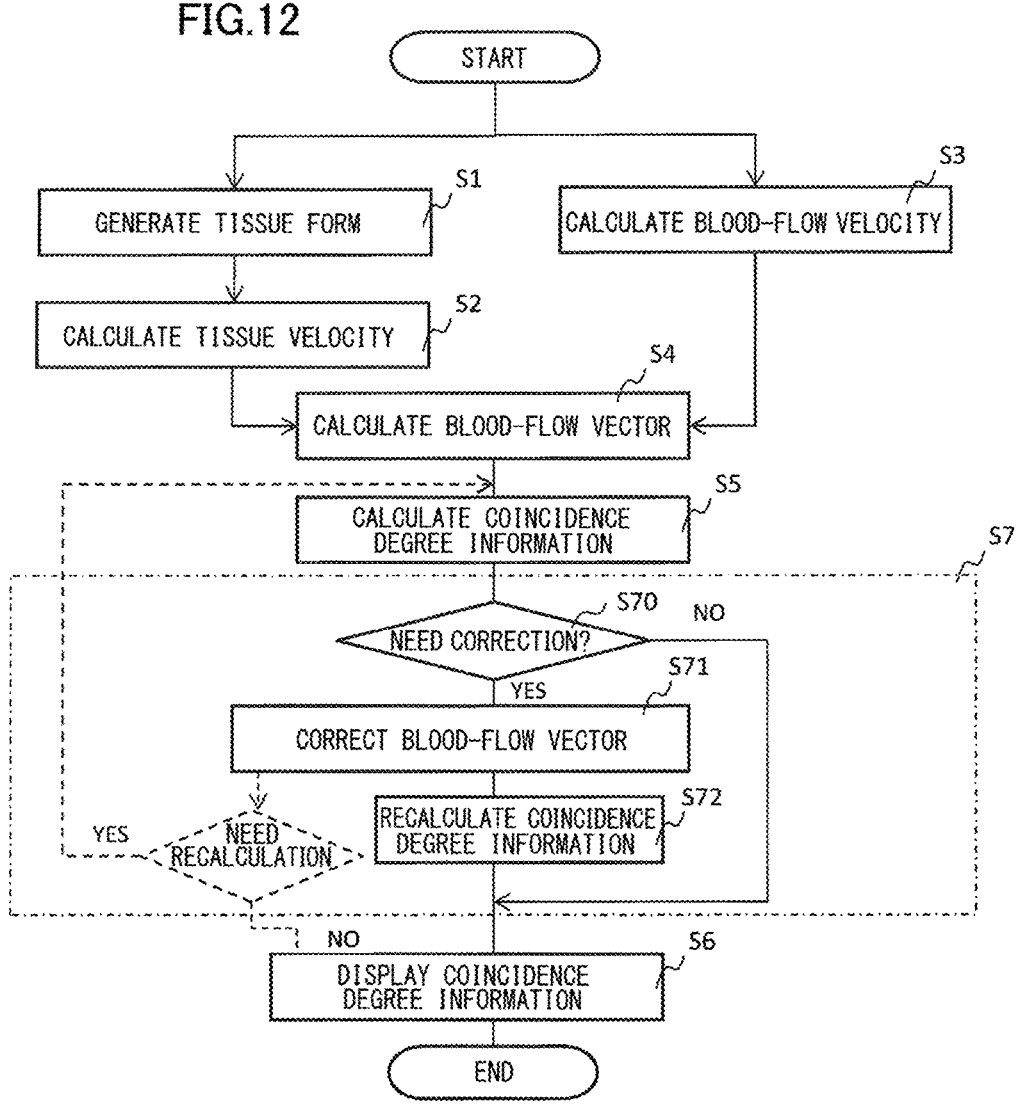
FIG. 12 is a flowchart illustrating the operation of the signal processor according to the second embodiment.

FIG. 12 illustrates the operation of the present embodiment. In FIG. 12, the steps indicating the same operations as those of the first embodiment in FIG. 2, are labeled the same, and tedious explanation will not be made.

Also in the present embodiment as illustrated in FIG. 12, each of the steps from S1 go S6 as shown in FIG. 2 is performed, and the step S5 for calculating the coincidence degree includes the step S51 for calculating the coincidence degree and the step S52 for the statistical processing as shown in FIG. 6, in the same manner as the first embodiment or a modification example thereof. The present embodiment is characterized in that the step S5 further includes the step S7 for correcting the velocity vector, by using the coincidence degree A calculated in the step S51 and the average $E_A$ of the coincidence degrees calculated in the step S52. Correction of the velocity vector may be realized by a correction part that is added to the signal processor 15 as shown in FIG. 1, or by the coincidence degree estimator 155.

<Step S51>

Correction of the velocity vector includes the step S71 for correcting the velocity vector, and the step S72 for recalculating the coincidence degree by using the corrected velocity vector.

<Step S51>

The average $E_A$ of M coincidence degrees $A_{b,j}$ calculated in the step S51 may be a bias error of the entire velocity vectors calculated in the color Doppler imaging (step S3), and the bias error may be divided into errors of individual vectors. Each velocity vector (velocity component in the orthogonal direction) calculated by the velocity vector estimation step S4 is corrected according to the following formula 17:

[Formula 17]

$$v_{i,j}^{mod} = v_{i,j}^m - E_A \frac{j}{N} \tag{17}$$

In the formula, the suffix "mod" of the velocity vector on the left-hand side represents a corrected value (the same in the following description).

The correction may be applied only when the bias error is remarkable, or the correction may be applied to all the cases so as to assure the accuracy. It is possible to determine whether the bias error $E_A$ is remarkable or not, for example, by the rate of error to the velocity component, and when the rate of error exceeds a predetermined range, it is determined as remarkable. The step S7 may be performed only when it is determined as remarkable (step S70) or the correction may be applied to all the cases. Then, the velocity vector being corrected (orthogonal component) and the velocity component in the beam direction are used to correct the velocity vector. The corrected velocity vector is displayed on the screen in the step S6.

<Step S51>

By using the velocity vector being corrected (orthogonal component), in the similar manner as the step S5, the coincidence degree $A_b^{mod}(r)$ or $A_a^{mod}(r)$ is recalculated according to the formula 7 or 8, and the resultant average $E_A$ and the dispersion σ are used to calculate the certainty E.

[Formula 18]

$$E = E_A^{mod} \pm t \frac{\sigma_A^{mod}}{\sqrt{N}} \tag{18}$$

From the certainty E recalculated according to the formula 18, the reliability B of the corrected velocity vector is calculated. Calculation of the reliability B follows the aforementioned formula 15, and a maximum value, a minimum value, an average, or a dispersion, of $v_{i,j}^{mod}$, a combination thereof, or a measured velocity range, may be used as U (a representative value of the velocity) in the formula 15. The reliability B is displayed together with the corrected velocity vector on the screen. Similar to the first embodiment, as illustrated in the figures from FIG. 9 to FIG. 11, various display modes may be applicable, such as the numerical value display, the lamp display, and the comment display.

According to the present embodiment, on the basis of the coincidence degree of the velocity vectors obtained by two methods, the velocity vector is corrected, thereby enhancing the precision in estimating the velocity vector, and expecting reduction of the bias error.

In the present embodiment, it is explained that the velocity vector is corrected by using the average $E_A$ (bias error) of the coincidence degrees. It is further possible to correct the velocity vector by using the coincidence degree itself according to the formula 19.

[Formula 19]

$$v_{i,j}^{mod} = v_{i,j}^m - A_{b,i} \frac{j}{N} \tag{19}$$

In this case, even though recalculation is carried out by using the corrected velocity vector, there is no change in the coincidence degree, and therefore, the step S72 is not performed.

In the same manner as the step S5, the certainty E is calculated as the following, by using the corrected velocity vector (orthogonal component).

[Formula 20]

$$E = \pm t \sigma_v^{mod} \tag{20}$$

In the formula 20, $\sigma_v^{mod}$ represents the dispersion of errors $\Delta v_{i,j}^{mod}$ in the individual corrected vectors, and it is obtained as the following:

[Formula 21]

$$\sigma_v^{mod} = \frac{\sigma_A}{C^{mod}} \tag{21}$$

In the formula 21, $C^{mod}$ represents a constant between or equal to 2 and 3. Here, $C^{mod}$ has a value of $\sqrt{6}$, if it is assumed that an error factor of $\Delta v_{i,j}$ holds a Gaussian probability density function. In this situation, the error is described as the following:

[Formula 22]

$$E = \pm t \frac{\sigma_A}{\sqrt{6}} \tag{22}$$

Further in the present embodiment, when the steps S71 and S72 are performed, it is possible to further repeat the step S71 for correcting the velocity vector and the step S72 for recalculating the certainty, after reflecting the result of the step S72. FIG. 12 illustrates this situation by the dotted line. This configuration may raise the precision in estimating the velocity vector. It is to be noted that modifications applied to the first embodiment may be similarly applicable to the present embodiment.

Third Embodiment

Figure 13:
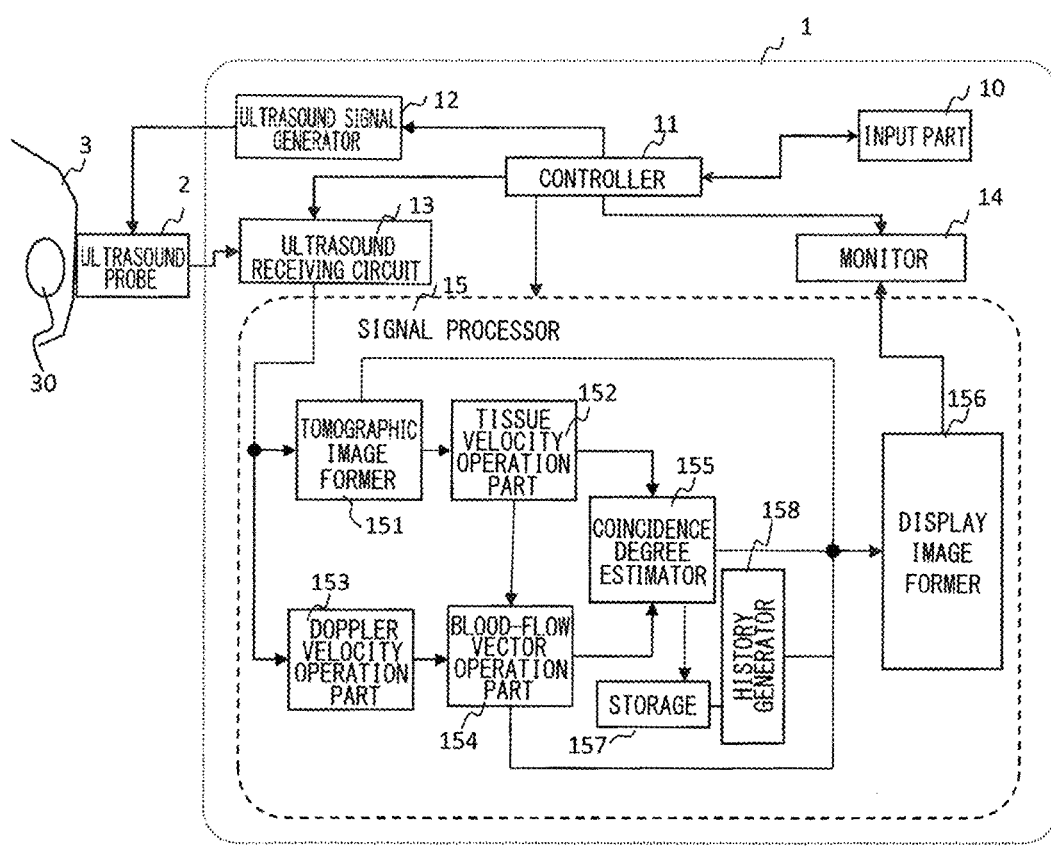
FIG. 13 is a block diagram showing a configuration example of the ultrasound diagnostic apparatus according to the third embodiment.

The present embodiment is characterized in that it is provided with a function to store history of the coincidence degrees and the certainty calculated in the first or the second embodiment, and display a result of temporal variation. FIG. 13 illustrates a configuration example of the ultrasound diagnostic apparatus of the present embodiment. In this configuration example, the signal processor 15 is provided with a storage 157 configured to store information such as the coincidence degree, certainty, and reliability (hereinafter, referred to collectively as coincidence degree information) calculated by the velocity coincidence degree estimator 155, and a history generator 158 configured to generate history information by using the coincidence degree information acquired at different times, being stored in the storage 157.

Figure 14:
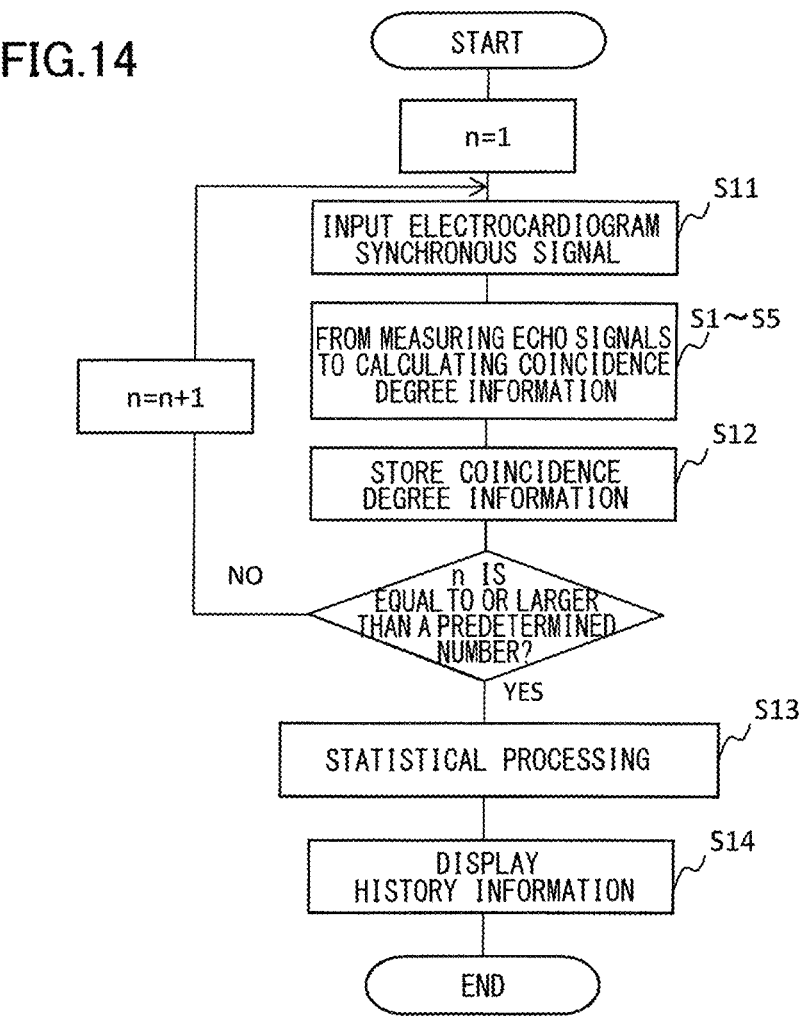
FIG. 14 is a flowchart illustrating the operation of the signal processor according to the third embodiment.

Other configurations are the same as those of the ultrasound diagnostic apparatus as shown in FIG. 1, and tedious explanations will not be made. With reference to FIG. 14, operations of the present embodiment will be explained. In the present embodiment, firstly an electrocardiogram synchronous signal is inputted in the step S11, and thereafter, the operations from the steps S1 to S5 as shown in FIG. 2, for instance, are repeated at various timing. As explained in the first embodiment, in the step S2, scanning is performed at different times so as to calculate the tissue velocity. Information items obtained by the scanning at different times may be used in the repetition in the step S11-S12. The operations are repeated with each heartbeat, or at intervals of plural heartbeats. Alternatively, the repetition may be performed by selectively extracting a characteristic time phase, such as a contraction phase or a diastolic phase of the heart. Electrocardiogram signals that are taken in from the input part 10 are used as the information indicating the heartbeats or the time phase (step S11).

The average $E_A$ and deviation σ in the beam direction of the velocity coincidence degrees calculated and estimated according to two methods are obtained every time the measurement is performed, and they are stored in the storage 157 (step S12). A series of processing in the steps S11, from S1 to S5, and S12 are repeated until reaching the count which allows statistical processing (until n becomes a predetermined number).

Figure 15A:
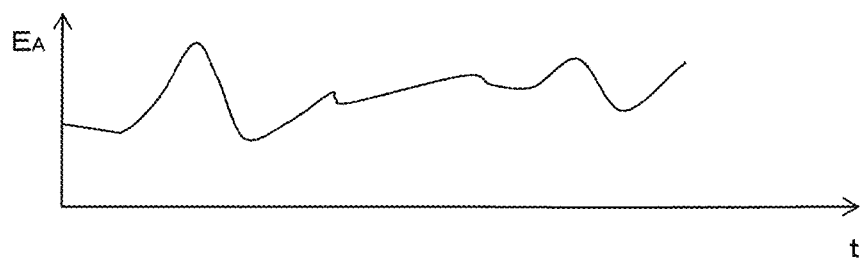
FIG. 15($a$) and FIG. 15($b$) illustrate examples of history information.
Figure 15B:
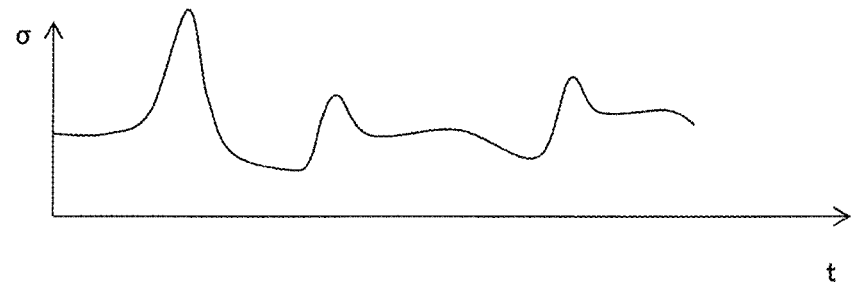

The history generator 158 uses the coincidence degree information accumulated in the storage 157 to generate a graph indicating the temporal variation as shown in FIG. 15, as to each of the coincidence degree and the deviation, and calculates the maximum coincidence degree $E_A^{max}$, the minimum coincidence degree $E_A^{min}$, and the average coincidence degree $E_A^{ave}$ (step S13). Those values are displayed on the screen, together with the graph (step S14).

The time information of the coincidence degree may indicate in which cardiac time phase, the velocity vector with high reliability is obtained, by checking whether or not there is a correlation with the cardiac time phase, if the operations are repeated without changing the tilt of the probe. In contrast, when the operations are repeated with varying the probe tilt, the time information may indicate at which angle the velocity vector with high reliability is obtained. If the coincidence degree remains low even though the probe angle is changed, the time information may indicate that there may be a problem in cardiac function.

According to the present embodiment, temporal statistical processing is added to the coincidence degree information, and it is possible to provide effective information as an index for the examination.

As described above, preferred embodiments of the present invention have been explained. A major feature of the present invention is to establish the certainty/reliability of the blood-flow velocity information (two-dimensional blood-flow velocity information) being estimated in the blood flow mapping display, and the method for obtaining the blood flow velocity is not limited to those embodiments as described above. By way of example, in the present embodiment, as one method for obtaining the blood flow velocity, an explanation has been made on the method that uses the equation of continuity of the two-dimensional flow and the tissue blood-flow boundary velocity and at one position out of two positions, so as to estimate the velocity at the other position. It is further possible to employ a publicly known blood-flow velocity calculation method, such as a method that corrects the angle with respect to the velocity information in the Doppler beam direction so as to estimate the velocity.

Furthermore, the display of the reliability may utilize a publicly known announcing means such as sound, instead of the screen display, or together with the screen display. One of the examples for formulating the certainty in the present invention is to perform certainty formulation on the basis of the coincidence degree of the blood flow velocities being calculated or estimated by two different methods. However, this index regarding the certainty on the basis of the coincidence degree may not be limited to the examples above.

In addition, the device configurations as shown in FIG. 1 and FIG. 13 are just examples, and various configurations may be applicable as far as the characteristic functions of the present invention are achievable. It is possible to remove partial elements that do not have any influence on achieving the characteristic functions, from the configuration shown in FIG. 1 or FIG. 13, or they may be configured as a different module.

INDUSTRIAL APPLICABILITY

In the ultrasound diagnostic apparatus that is able to estimate blood-flow velocity information in the blood flow mapping display, reliability as an estimation result is displayed on the screen, thereby contributing to more assured diagnosis.

EXPLANATION OF REFERENCES

1 . . . DEVICE MAIN BODY 2 . . . ULTRASOUND PROBE, 10 . . . INPUT PART, 11 . . . CONTROLLER, 12 . . . ULTRASOUND SIGNAL GENERATOR, 13 . . . ULTRASOUND RECEIVING CIRCUIT, 14 . . . MONITOR, 15 . . . SIGNAL PROCESSOR, 151 . . . TOMOGRAPHIC IMAGE FORMER, 152 . . . TISSUE VELOCITY OPERATION PART, 153 . . . DOPPLER VELOCITY OPERATION PART, 154 . . . BLOOD-FLOW VECTOR OPERATION PART, 155 . . . COINCIDENCE DEGREE ESTIMATOR (ESTIMATOR), 156 . . . DISPLAY IMAGE FORMER, 157 . . . STORAGE, 158 . . . HISTORY GENERATOR

What is claimed is:
1. An ultrasound imager comprising,
an ultrasound probe configured to transmit an ultrasound wave to an examination target and receive an echo signal reflected from the examination target,
a signal processor configured to process the echo signal received by the ultrasound probe, and
a monitor configured to display a processing result from the signal processor,
the signal processor comprising,
an operation part configured to estimate blood-flow velocity information from the echo signal, an image former configured to display blood-flow information by mapping, on the basis of the blood-flow velocity information being estimated, and
an estimator configured to obtain a certainty degree of the blood-flow velocity information displayed by the mapping using a degree of coincidence derived from a first blood-flow velocity calculated from the echo signal according to a tissue velocity method and a second blood-flow velocity calculated from the echo signal according to a Doppler velocity method and based, at least in part, on the obtained certainty degree, determine whether to:
generate a corrected blood-flow velocity information,
re-calculate the degree of coincidence based on the corrected blood-flow velocity information, and
transmit the corrected blood-flow velocity information and the certainty degree to be displayed by the image former, wherein the image former replaces the displayed blood-flow information with the corrected blood-flow information and generates a displayable notification of the re-calculated degree of coincidence, wherein a user prompt is displayed if the degree of coincidence is not within an acceptable range.

2. The ultrasound imager according to claim 1, wherein, the operation part comprises a blood-flow vector operation part configured to estimate a blood-flow vector representing a flow of blood, from the echo signal, and the estimator obtains the certainty degree of the blood-flow vector being estimated, on the basis of the degree of coincidence between the first blood-flow velocity, and the second blood-flow velocity.

3. The ultrasound imager according to claim 1, wherein, the signal processor comprises,
a tissue tomographic image former configured to generate a tissue tomographic image from the echo signal,
a first velocity operation part configured to calculate the first blood-flow velocity as to a predetermined portion on the basis of the tissue tomographic image that is generated by the tissue tomographic image former,
a Doppler velocity operation part configured to calculate a Doppler velocity from the echo signal by using the Doppler effect, and
a second velocity operation part configured to calculate the second blood-flow velocity of the predetermined portion, by using the Doppler velocity, and
the estimator comprises a coincidence degree estimator configured to estimate the degree of coincidence between the first blood-flow velocity and the second blood-flow velocity calculated on the predetermined portion.

4. The ultrasound imager according to claim 1, wherein, the first blood-flow velocity is a tissue blood-flow boundary velocity calculated on the basis of temporal variation of a tissue position in a tissue tomographic image, and the second blood-flow velocity is obtained by using the Doppler velocity that is calculated from the echo signal by using the Doppler effect.

5. The ultrasound imager according to claim 1, wherein, the first blood-flow velocity and the second blood-flow velocity each corresponds to a blood-flow velocity vector in the direction orthogonal to a beam direction of an ultrasound beam that is outputted from the ultrasound probe, or a blood-flow velocity vector obtained by combining a velocity component in the beam direction with the velocity component in the orthogonal direction.

6. The ultrasound imager according to claim 1, wherein, the estimator calculates any of the following values as the coincidence degree; a difference between the blood-flow velocity vectors at an identical portion, a ratio between the blood-flow velocity vectors at the identical portion, a rate of the difference between the blood-flow velocity vectors at the identical portion, and an amount obtained by applying statistical processing to the values.

7. The ultrasound imager according to claim 1, wherein, the estimator applies statistical processing to plural coincidence degrees, and calculates the certainty degree of the blood-flow velocity information.

8. The ultrasound imager according to claim 7, wherein, the estimator uses a central limit theorem to calculate an average and a dispersion of the plural coincidence degrees, and calculates the certainty degree on the basis of the average and the dispersion of the coincidence degrees.

9. The ultrasound imager according to claim 7, wherein, the plural coincidence degrees processed by the estimator are made up of spatially and/or temporally various plural coincidence degrees.

10. The ultrasound imager according to claim 9, wherein, each of the temporally various plural coincidence degrees has a different cardiac cycle or a different cardiac time phase of the heart.

11. The ultrasound imager according to claim 7, wherein, the estimator comprises a storage configured to store history of the plural coincidence degrees, and calculates an average value, dispersion, a maximum value, or a minimum value of the plural coincidence degrees.

12. The ultrasound imager according to claim 7, wherein, the estimator uses a result of the statistical processing so as to correct the blood-flow velocity information that is estimated by the operation part.

13. The ultrasound imager according to claim 12, wherein, the signal processor uses the blood-flow velocity information being corrected to recalculate the second blood-flow velocity, and obtains the certainty degree of the blood-flow velocity information being corrected.

14. The ultrasound imager according to claim 1, wherein, the monitor displays the certainty degree of the blood-flow velocity information.

15. The ultrasound imager according to claim 14, wherein, the monitor displays as the certainty degree, a numerical value, colors indicating plural stages, or measures to be taken by an examiner in the form of comments.

16. The ultrasound imager according to claim 14, wherein, the monitor displays the certainty degree of the blood-flow velocity information, together with a tomographic image and/or a blood-flow vector.

17. An ultrasound imaging method that forms a tomographic image by using ultrasound echo signals reflected from an examination target, and displays a blood-flow mapping, comprising the steps of,
calculating blood-flow velocity information from the echo signal and displaying the blood-flow velocity information by mapping,
calculating a blood-flow velocity at a predetermined location by using the echo signal, according to a tissue velocity method,
calculating a blood-flow velocity at the predetermined location by using the echo signal, according to a Doppler velocity method,
calculating a degree of coincidence using a difference between the blood-flow velocity calculated according to the tissue velocity method and the blood-flow velocity calculated according to the Doppler velocity method, and obtaining a certainty degree of the blood-flow velocity information displayed by the mapping on the basis of the coincidence degree and upon determining that the obtained certainty degree exceeds a predetermined range:
generating a corrected blood-flow velocity information,
re-calculating the degree of coincidence based on the corrected blood-flow velocity information, and
transmitting the corrected blood-flow velocity information and the certainty degree to be displayed by the image former, wherein the image former replaces the displayed blood-flow information with the corrected blood-flow information and generates a displayable notification of the re-calculated degree of coincidence, wherein a user prompt is displayed if the degree of coincidence is not within an acceptable range.

18. The ultrasound imaging method according to claim 17, wherein, the step of obtaining the certainty degree of the blood-flow velocity information calculates the coincidence degrees as to plural positions, and obtains the certainty degree according to statistical processing.

19. The ultrasound imaging method according to claim 17, further comprising the step of displaying and/or announcing the certainty degree of the blood-flow velocity information.

* * * * *